United States Patent [19]

Andersson et al.

[11] Patent Number: 5,385,904
[45] Date of Patent: Jan. 31, 1995

[54] ORGANIC SALTS OF N, N'-DIACETYL CYSTINE

[75] Inventors: Carl-Magnus A. Andersson, Lund; Håkan S. A. M. Bergstrand, Bjärred; Edib Jakupovic, Nykvarn; Bo-Göran Josefsson; Magnus L. Lindvall, both of Lund; Bengt O. Särnstrand, Bjärred; Eric N. G. Teneberg, Södertälje, all of Sweden

[73] Assignee: Aktiebolaget Astra, Sodertalje, Sweden

[21] Appl. No.: 981,373

[22] Filed: Nov. 25, 1992

[30] Foreign Application Priority Data

Nov. 29, 1991 [SE] Sweden ................................. 9103572

[51] Int. Cl.⁶ .............................................. A61K 31/495
[52] U.S. Cl. .................................... 514/255; 514/554; 514/562; 544/357; 544/358; 562/557
[58] Field of Search ............... 562/557; 514/562, 255, 514/554; 544/358, 357

[56] References Cited

U.S. PATENT DOCUMENTS

| | | | |
|---|---|---|---|
| 3,647,834 | 3/1972 | Martin | 562/557 |
| 3,878,305 | 4/1975 | Damico | 562/557 |
| 3,952,115 | 4/1976 | Damico | 562/557 |
| 4,093,739 | 6/1978 | Martin | 562/557 |
| 4,141,734 | 2/1979 | Lenoir | 562/557 |
| 4,241,086 | 12/1980 | Iwao | 562/557 |
| 4,708,965 | 11/1987 | Morgan | 514/563 |
| 4,724,239 | 2/1988 | Morgan | 562/557 |
| 4,801,579 | 1/1989 | Rainer | 562/557 |
| 4,827,016 | 5/1989 | Morgan | 560/16 |
| 4,859,653 | 8/1989 | Morelle | 562/557 |

FOREIGN PATENT DOCUMENTS

| | | |
|---|---|---|
| 0300100 | 1/1989 | European Pat. Off. . |
| 2503151 | 4/1981 | France . |
| 155298 | 12/1981 | Japan . |
| 62-195356 | 8/1987 | Japan ................ 562/557 |
| 9118594 | 12/1991 | WIPO . |
| 9221362 | 12/1992 | WIPO . |

OTHER PUBLICATIONS

Marshall, et al. "Preparation and Properties of the Isomeric Forms of Cystine and S-Benzylpenicillamine", J. Amer. Chem. Soc. 79: 4538–4544, 1957.

Greenstein, et al. "Ammonia Formation from Cystine Peptides and Dehydropeptides in Rat Liver Digests", Arch. of Biochem. 18: 377–382, 1948.

Dialog Information Services Accession No. 2936022, File 351 World Patents Index Acc. No.: 82-00887E/01, "Shampoo compsn. contg. salt ... with basic aminoacid or their mixt." Jul. 5, 1986.

*Primary Examiner*—Michael L. Shippen
*Attorney, Agent, or Firm*—White & Case

[57] ABSTRACT

New crystalline organic salts of N,N'-diacetyl cystine with immunomodulating effect, processes for their preparation, pharmaceutical compositions containing them and methods of their pharmacological use.

6 Claims, No Drawings

ORGANIC SALTS OF N, N'-DIACETYL CYSTINE

FIELD OF THE INVENTION

The present invention relates to organic salts of N,N'-diacetyl cystine, in the following referred to as DiNAc, with immunomodulating activity as well as pharmaceutical compositions based on these salts and methods for their pharmacological use. The invention specifically concerns methods to obtain crystalline, non-hygroscopic and chemically stable salts containing non-toxic organic cations, which are useful for therapy of diseases where a defect in the immune system is indicated.

BACKGROUND ART

N-Acetyl-L-cysteine is a well known compound which is routinely used as a therapeutic agent against chronic obstructive diseases and chronic bronchitis. Although the first patent was filed in 1964 (GB 954268) the mechanism of action of the compound has not been established. It has recently been discovered that the corresponding disulfide of N-Acetyl-L-cysteine, i.e. L-DiNAc, acts as a potent immunostimulator (Swedish patent application no SE 9002067-8), showing an activity comparable to contemporary immunostimulants such as sodium diethyl dithiocarbamate or 2,2'-dithiobisethanol.

Routes for the preparation of DiNAc have been reported in several patents (U.S. Pat. Nos. 4,827,016, 4,724,239 and 4,708,965, European Patent No 300100 and German Patent No 2326444). DiNAc is, however, amorphous and hygroscopic, so that it is difficult to isolate and formulate into pharmaceutical compositions and its administration is normally only in the form of aqueous solutions. Most salts of DiNAc with inorganic or organic cations share the same unfavourable physical properties with the free diacid. Examples of salts of other, sulfur-containing, amino acids have appeared in the patent literature (U.S. Pat. No 3,647,834, JP patent No 56155298 and FR patent No 8106592)

DISCLOSURE OF THE INVENTION

We have now surprisingly found that a few salts of DiNAc with organic bases exhibit a favourable combination of non-hygroscopicity and crystallinity which permits the isolation and formulation of these salts in solid form and allows them to be administered by inhalation in solid form, or in other dry formulations, should this be clinically desirable.

The present invention provides organic salts of DiNAc, having the formula Ia or Ib:

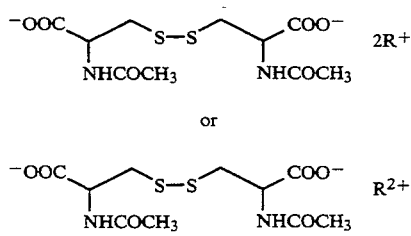

where $R^+$ and $R^{2+}$ is a mono- or diprotonated organic amine respectively. The organic amine is selected from lysinium, ethylenediaminium, N,N'-dibenzylethylenediaminium, N-benzyl-2-phenylethylaminium, piperazinium and 1-adamantanaminium.

Lysinium can be in its D- or L-form. Most preferred is the L-form.

The invention includes hydrated and solvated salts, e.g. solvated with lower alkanals. The invention includes salts of DiNAc in its individual isomers, i.e. D-, L- and meso-forms as well as in its racemic form. Most preferred are the L-forms of these salts.

We have found that the new salts of the invention fulfil the requirements of ease of crystallization, non-hygroscopicity and chemical stability while still retaining the immunomodulating activity of DiNAc, and are thus medically useful.

This invention thus provides compounds with advantageous properties for the treatment of diseases where an anergy of the immune response or an aberrant immune response or an ineffective host defence can be suspected. Such diseases include chronic bronchitis, where a reduction of the rate of exacerbations has previously been reported with immune response modifiers such as Biostim (Radermecker, M. et al. Int. J. Immunopharmac. 10, 913-917, 1988; Scheffer, J. et al. Arzneim. Forsch/Drug Res. 41,815820, 1991), Ribomunyl and BronchoVaxom (Paupe, J. Respiration 58, 150-154, 1991) as well as with N-Acetylcysteine (See Bergstrand, H. et al J. Free Radic. Biol. Med. 2, 119-127, 1986).

Such diseases also include certain forms of malignant diseases. Thus, numerous research institutes round the world aim at finding ways of stimulating the immune response of patients with various forms of malignant diseases and numerous reviews in the literature deal with this approach (Stevenson, F. K. FASEB J 5: 2250-2257, 1991). To mention one example patients with intracranial tumours (gliomas) exhibit a profound decrease in immunity possibly due to a defect in the secretion of IL-2 as well as the expression of IL-2 receptors in T cells from such patients (Roszman, T. et al. Immunology Today 12, 370 374, 1991). Moreover, a significant adjuvant effect in immunotherapy of melanoma and colon carcinoma has been documented for the immunostimulator Levamisole (Van Wauwe, J. and Janssen, P. A. J. Int J. Immunopharmac. 13, 3-9, 1991) and immunotherapy with IL-2 in vivo or treatment of patients lymphokine activated killer cells with IL-2 ex vivo has caused the regression of cancer in selected patients (Rosenberg, S. A. Immunology Today 9, 58-, 1988). The malignant diseases at which the compounds I can be expected to have advantageous effects include tumours of mesenchymal origin such as sarcomas like fibrosarcoma, myxosarcoma, liposarcoma, chondrosarcoma, osteogenic sarcoma or chordosarcoma, sarcomas like anglosarcoma, endotheliosarcoma, lymphangiosarcoma, synoviosarcoma or mesotheliosarcoma, leukemias and lymphomas like granulocytic leukemia, monocytic leukemia, lymphocytic leukemia, malignant lymphoma, plasmocytoma, reticulum cell sarcoma or Hodkins disease, sarcomas like leiomyosarcoma or rhabdomysarcoma, tumours of epithelial origin (Carcinomas) like squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma-cholangiocarcinoma, transitional cell carcinoma, choriocarcinoma, semonoma or embryohal carcinoma, tumours of the central nervous system like glioma, meningoma, medulloblastoma, schwannoma or ependymoma.

Moreover, the compounds also have advantageous properties for treatment of chronic infections such as herpes, aphtous stomatitis and minimal change syndrome where clinical improvement has previously been reported by treatment with an immunostimulator such as Levamisole as well as other chronic inflammatory diseases in the urinary tract or in ear, nose or throut, which benefit from treatment with immunostimulators such as Biostim, Broncho-Vaxom and Ribomunyl, or an HIV infection or AIDS.

Moreover, an impairment, a defect or an imbalance of the immune response has also been postulated to exist at atopic diseases such as atopic dermatitis, rhinitis and asthma (Katz, D. H. Transplantation Reviews 41, 77-108, 1977). Since theoretical considerations suggest that stimulation of an immune response would possibly be the best way of restoring imbalances and autoimmunity (Varela, F. J. and Coutinho, A. Immunology Today 12, 159-166, 1991), the compounds can also be expected to have advantageous properties for treatment of asthma, rhinitis, atopic dermatitis and autoimmune diseases like non-obese diabetes, systemic lupus erythematosus, sclerodermia, Sjögren's syndrome, dermatomyositis or multiple sclerosis, rheumatoid arthritis and possibly psoriasis.

Moreover, the compounds, due to their immune stimulating properties, can be expected to have advantageous properties as adjuvants in various forms of vaccine preparations.

Finally, the compounds can be expected to have advantageous properties for treatment of atherosclerosis whether or not it will influence a putative inflammatory process in this condition (Hansson. G. K. et al. Proc. Nat. Acad. Sci. USA 88,10530, 1991).

The importance of immunostimulatory drugs on rumour outgrowth is illustrated in our relevant tumour outgrowth test systems. The experimental rat rumour models described below reflect very well the tumourostatic potency of the compounds of this invention in comparison with the well established immunostimulatory drug Levamisole, and they reflect clinically very well a fastly growing rumour, the mammary carcinoma, and a slowly progressively growing tumour, the glioma, and in both systems the drug has an excellent static effect on rumour outgrowth.

Particularly suitable for treatment with the compounds of this invention are: Malignancies such as melanoma, mammary carcinoma, gastrointestinal carcinoma, glioma, bladder carcinoma and squamous cell carcinoma of the neck and head region;

Infections such as chronic bronchitis, hepatitis, post-infectious anergy and aquired immune deficiencies such as AIDS;

Posttraumatic immunological anergy, and

Purported autoimmune diseases such as rheumatoid arthritis, multiple sclerosis and psoriasis.

Effective doses for treatment of the diseases above are in the range of 0.1-100 mg, preferably 1.0-60 mg daily.

Methods of Preparation

The organic salts of formula Ia and Ib are generally prepared by mixing DiNAc and the organic base, as defined above, each dissolved or dispersed in a solvent or solvent mixture. Solvents such as water, alcohols, glycols, ketones, amides, sulphoxides or other polar solvents or solvent mixtures may be used. The salt either precipitates directly from the reaction mixture, or is obtained by the addition of a less polar solvent or by evaporation or lyophilisation. The reaction is performed at elevated temperature or room temperature, depending on the solubility in the medium. Alternatively, the salt can be prepared by oxidation of the appropriate N-acetyl cysteine salt in aqueous or alcoholic solution, followed by precipitation as above. The oxidation may be effected either chemically, using e.g. hydrogen peroxide or halogen, or electrochemically.

Pharmaceutical Formulations

According to the present invention the compounds of the formula Ia and Ib can be formulated for administration by inhalation as well as by other routes, e.g. orally or topically with or without a pharmaceutically acceptable carrier.

The substance can be inhaled from a pressurized metered dose inhaler, from a dry powder inhaler, e.g. Turbuhaler ® or from a dry powder inhaler utilizing gelatine, plastic or other capsules. Non-toxic and chemically inert substances e.g. lactose, trehalose, mannitol or glucose, can be added to the powdered substance.

The substance can also be administered orally in the form of capsules or tablets where the capsule, the tablet or the active substance itself can be coated or non-coated. This coating may consist of for example hydroxypropyl cellulose and aerosil in isopropanol or other suitable solvents. A non-toxic and chemically inert substance can be added to the powdered substance in order to obtain desirable physical or pharmaceutical properties.

Parenteral administration of the new compounds is also possible.

Pharmacological Experiments

The ability of the compound di-L-lysinium-N,N'-diacetyl-L-cystinate (Ia; R=lysine) to modulate immune responses is illustrated by its efficacy in the animal delayed type hypersensitivity (DTH) test in the mouse.

Both male and female Balb/c mice, obtained from Bomholtsgaard (Denmark), were used at the weight of 18-20 gram. 4-Ethoxymethylene-2-phenyloxazolin-5-one (OXA) was purchased from BDH (England) and served as the antigen in this test.

The mice were sensitized, Day 0, by epicutaneous application of 150 µl of an absolute ethanol-acetone (3:1) solution containing 3% OXA on the shaved abdomen. Treatment with the disulphide salt or vehicle (0.9% NaCl) was initiated by oral feeding immediately after sensitization and continued once daily until Day 6. Seven days (Day 6) after the sensitization, both ears of all mice were challenged on both sides by topical application of 20 µl 1% OXA dissolved in peanut oil. Ear thickness was measured prior to and 24 or 48 hours after challenge using an Oditest spring calliper. Challenges and measurements were performed under light pentobarbital anaesthesia.

The intensity of the DTH reactions was expressed according to the formula: $T_{t24/48}$-$Tt_0$ µm units, where t0, t24 and t48 represent the ear thickness before and 24 or 48 hours after challenge respectively, in individual tests (T). The results were expressed as the mean ±S.E.M. The level of significance between means of the groups was obtained by Student's two-tailed t-test. Tables 1 and 2 show the results from 24 and 48 hours measurements respectively, from a representative experiment. The immunostimulating potency of the compound is reflected in a significant difference in the increase in ear thickness as compared to the control. Thus, in treated animals, after 24 h the response was about twice that of the control animals (15 μm compared to 8 μm, Table 1).

TABLE 1

Ear thickness 24 hours after challenge of animals treated with the indicated doses of di-L-lysinium-N,N'-diacetyl-L-cystinate or vehicle (NaCl).

| Dose μmol/kg | N | Diff. | S.E.M. | $T_{24}-T_{t0}$ | Sign. |
|---|---|---|---|---|---|
| NaCl | 10 | 8.25 | 0.56 | | |
| 0.03 | 10 | 15.00 | 0.42 | | *** |
| 3.0 | 10 | 15.80 | 0.77 | | *** |

$P < 0.001$.

TABLE 2

Ear thickness 48 hours after challenge of animals treated with the indicated doses of di-L-lysinium-N,N'-diacetyl-L-cystinate or vehicle (NaCl).

| Dose μmol/kg | N | Dim. | S.E.M. | $T_{48}-T_{t0}$ | Sign. |
|---|---|---|---|---|---|
| NaCl | 10 | 8.83 | 0.31 | | |
| 0.03 | 10 | 12.55 | 0.41 | | *** |
| 3.0 | 10 | 13.20 | 0.28 | | *** |

$P < 0.001$.

The ability of the same test compound (Ia, R=lysine) to prolong or increase the survival of rats suffering from tumours is illustrated by two different experiments with tumour inoculation in rats.

Two groups each consisting of ten rats of the Wistar Furth strain were inoculated subcutaneously with $10^4$ mammary carcinoma cells per rat and tumour size was measured twice a week. In one group the rats were drinking ordinary water and in the other group the test compound dissolved in water so as to result in a dose of 0,03 μmol/kg/day of animal weight. After 38 days one animal from the water-drinking group was still alive while from the group which was given the compound seven animals were alive.

In another experiment three groups each consisting of ten rats of the Lewis strain were inoculated subcutaneously with $10^6$ glioma cells per rat and tumour size was measured twice a week. In one group the rats were drinking ordinary water and in the second group the test compound dissolved in water so as to give a dose of 0,03 μmol/kg/day of animal weight, while in the third group the rats were drinking water containing Levamisole, a well-known cancer therapeutic drug also at a dose of 0,03 μmol/kg/day of animal weight. After 119 days there was no surviving rat in the water-drinking group. In the group, which was given the test compound, six rats were still alive while in the group, which received Levamisole, three rats were alive after 119 days.

In both experiments with tumours there was a lower frequency of tumour positive animals and in both experiments there was an inhibition of tumour growth of the developed tumours in the groups receiving the compound solubilized in water.

In another experiment two groups each consisting of eight SCID mice (mice with the immune defect Severe Combined Immunodeficiency Disease) were inoculated with $2*10^3$ mammary carcinoma cells and outgrowth was measured twice a week. In one group the mice were drinking ordinary water and in the second group the test compound dissolved in water so as to give a dose of 0.03 μmol/kg/day of animal weight. There were no significant differences between the groups concerning growth rate and incidence. This indicates that the compound has no direct effect on the tumour cells but acts via the immune apparatus.

In an animal model of lupus, experimental murine systemic lupus erythematosus (SLE), MRL Ipr/Ipr mice spontaneously develop lymphoid hyperplasia, dermatitis, arthritis and glomerulonephritis. The effect of di-L-lysinium-N,N'-diacetyl-L-cystinate on glomerulonephritis as proteinuria and hematuria also the survival rate of the animals, has been studied in this murine lupus model. Di-L-lysinium-N,N'-diacetyl-L-cystinate was administrated in the drinking water and the mean dosage was calculated to 0.03 μmol/kg/day. The control mice received tap water. Both groups had free access to the drinking water. The treatment started when the animals reached 8 weeks of age and continued until death or 46 weeks of age, when the study was ended.

The assessment of proteinuria and haematuria was performed by the usage of reagent strips, Eour-Test*, Boehringer Mannheim.

Upon administration of di-L-lysinium-N,N'-diacetyl-L-cystinate the survival rate was significantly improved compared to the control mice. The mortality rate for the untreated group (21 animals) reached 50% around 25 weeks of age. For the di-L-lysinium-N,N'-diacetyl-L-cystinate treated MRL-lpr/lpr mice (12 animals) this mortality rate was not reached until week 44.

This form of treatment also significantly improved the score for both proteinuria and haematuria measured as arbitrary units of the reagent strips, compared to the untreated group.

These results show the immunomodulating potency of the compounds of this invention, particularly with regard to SLE.

WORKING EXAMPLES

Pharmaceutical Formulations

The following examples are representative of pharmaceutical formulations intended for different modes of local and systemic administration.

Example 1 Pressurised Aerosol for Inhalation

The aerosol system is arranged so that each metered dose contains 0.1–1.0 mg.

| | |
|---|---|
| Compound Ia or Ib, micronized | 1.0% w/w |
| Sorbitan trioleate | 0.7% w/w |
| Trichloromonofluoromethane | 24.4% w/w |
| Dichlorotetrafluoroethane | 24.4% w/w |
| Dichlorodifluoromethane | 49.5% w/w |

Example 2. Powder Aersol for Inhalation of Pure Substance

Pure substance prepared for inhalation from Turbuhaler. Each single dose contains 0.1–1.0 mg.

| | |
|---|---|
| Compound Ia or Ib, processed | 0.1–1.0 mg |

Example 3. Powder Aerosol for Inhalation

Each single dose contains 0.1–1.0 mg in a capsule.

| | |
|---|---|
| Compound I, micronized | 0.1–1.0 mg |

-continued

| | |
|---|---|
| Lactose | 50 mg |

Example 4. Solution for Nebulising

The solution contains 1.0–10.0 mg/mL and 1–3 mL may be administered in a single dose.

| | |
|---|---|
| Compound I | 1.0–10.0 mg |
| Water for injection | to 1.0 mL |

Example 5. Tablets

Each tablet contains:

| | |
|---|---|
| Compound I | 0.1–100 mg |
| Maize starch | 50 mg |
| Lactose | 150 mg |
| Polyvidone | 7 mg |
| Microcrystalline cellulose | 20 mg |
| Magnesium stearate | 2 mg |

Example 6. Oral Solution

A single dose of 10 mL contains 10–100 mg.

| | |
|---|---|
| Compound I | 1–10 mg |
| Sorbitol 70% | 150 mg |
| Glycerol | 100 mg |
| Sodium benzoate | 1 mg |
| Flavour | q.s. |
| Water purified | to 1.0 mL |

Example 7. Tablet for Controlled Release 1 tablet:

| | |
|---|---|
| Compound I | 1–100 mg |
| Paraffin Special | 145 mg |
| Lactose Powder | 50 mg |
| Colloidal Silicon Dioxide | 5 mg |
| Ethylcellulose 10 cps | 13 mg |
| Ethanol 99,5 vol % | 85 mg |
| Magnesium Stearate | 2,5 mg |

Example 8. Granulate for Controlled Release 1 g of granulate:

| | |
|---|---|
| Compound I | 1–100 mg |
| Ethylcellulose Dispersion | 10 mg |
| Acetyltributylcitrate | 0,5 mg |
| Eudragit L 100-55 | 55 mg |
| Triethylcitrate | 5 mg |
| Talc | 30 mg |
| Water newly distilled | 350 mg |
| Pellets, neutral | to 1000 mg |

Example 9. Solution for Injection 1 mL in a single dose contains 1.0–10.0 mg

| | |
|---|---|
| Compound Ia or Ib | 1.0–10.0 mg |
| Sodium chloride | 8.9–7.7 mg |
| Water for injection | to 1.0 mL |

Example 10. Cream for Topical Application 1 g of cream contains:

| | |
|---|---|
| Compound I | 0.1–1 mg |
| White soft paraffin | 75 mg |
| Liquid paraffin | 10 mg |
| Cetostearyl alcohol | 75 mg |
| Cetomacrogol 1000 | 20 mg |
| Metagin | 0.8 mg |
| Propagin | 0.2 mg |
| Water, purified | to 1.0 g |

Example 11. Ointment for Topical Application 1 g of ointment contains:

| | |
|---|---|
| Compound I | 0.1–1 mg |
| Liquid paraffin | 150 mg |
| White soft paraffin | to 1.0 g |

Example 12. Ophthalmic Solution

One dose of 2 drops contains 0.01–0.1 mg of compound I

| | |
|---|---|
| Compound I | 0.1–1 mg |
| Benzalkonium chloride | 0.1 mg |
| Sodium chloride | 9.0 mg |
| Water, sterile | to 1.0 mL |

Chemistry

Example 13

Di-L-lysinium-N,N'-diacetyl-L-cystinate (Ia; R=H$_2$N(COOH)CH(CH$_2$)$_4$NH$_3$):

N-Acetyl-L-cysteine (22 mol, 3.59 kg) was dissolved in 2.6 L of deionized water. Sodium hydroxide 45% in water (22 mol, 1.92 kg) was added with stirring and temperature kept below 20° C. After adjusting the temperature to 5° C., hydrogen peroxide (11.0 mol, 0.95 L) was carefully added dropwise during 90 min. The temperature was not allowed to exceed 10° C. during this addition. To the resulting solution was added 9 L of activated strongly acidic cation exchanger. After stirring for 10 minutes the pH was 2.0 and the ion exchanger was filtered off. The filtrate contained 9.65 mol of N,N'-diacetyl-L-cystine, as determined by HPLC using a standard prepared from the pure substance. To this crude solution was added L-lysine (19.3 mol, 3.17 kg). The thick solution formed, was slowly added to 50 L of refluxing ethanol containing 0.23 kg of crystalline di-L-lysinium-N,N'-diacetyl-L-cystinate. After the addition, the slurry was allowed to cool and the crystals were filtered off. Washing with ethanol (8 L) and drying (vacuum, 40° C.) for 12 hours afforded 5.36 kg (90%) of the title substance as a white crystalline solid.

Physical data: Mp: 210° C. (dec); $[\alpha]_D^{25} = -70°$ (c=0.54, H$_2$O); $^1$H-NMR (D$_2$O) δ: 1.36–1.60 [4H, m, Lys γCH$_2$], 1.73 [4H, p, Lys δCH$_2$], 1.84–1.96 [4H, m, Lys βCH$_2$], 2.05 [6H, s, CH$_3$], 2.95 [2H, dd, CH$_2$S], 3.02 [4H, t, Lys εCH$_2$], 3.25 [2H, dd, CH$_2$S], 3.76 [2H, t, Lys αCH], 4.50 [2H, dd, CHN] $^{13}$C-NMR (D$_2$O δ: 24.27; 24.80; 29.24; 32.72; 41.89; 42.78; 52.96; 57.30; 176.53; 177.41; 179.74; Analysis: Calcd for C$_{22}$H$_{44}$O$_{10}$N$_6$S$_2$, C:42.8 H:7.2 N: 13.6 Found, C: 42.6 H: 7.4 N: 13.7; MS m/z=325 (MH+), m/z=471 (MLysH+), m/z=617 (MLys2H+).

Example 14

Ethylenediaminium-N,N'-diacetyl-L-cystinate (Ib; R=H3NCH2CH2NH3):

To N,N'-diacetyl-L-cystine (30.9 mmol, 10 g) dissolved in 20 mL of water was added ethylenediamine (61.8 mmol, 3.73 g) and ethanol (30 mL). The solution was concentrated to a thick paste which was redissolved in 80 mL of ethanol. Crystallisation occurred after 2 hours stirring at 10° C. Filtration and drying gave 6.2 g (45%) of the title compound.

Physical data: Mp 185.2°–192.4° C. $^1$H-NMR (D$_2$O) δ; 2.06 [6H, s, CH$_3$], 2.96[2H, dd, CH$_2$S], 3.26[2H, dd, CH$_2$S], 3.28 [4H, s, H$_3$N+CH$_2$CH$_2$N+H$_3$], 4.50 [2H, dd, CHN]. $^{13}$C-NMR (D$_2$O) δ: 24.78; 39.99; 42.74; 56.98; 176.55; 179.82; Analysis: Calcd C: 37.5, H: 6.3, N: 14.6, S: 16.7. Found, C: 37.3, H: 6.8, N: 15.3, S: 15.2; MS m/z=385 [M(H$_2$NCH$_2$CH$_2$NH$_2$)H+]

Example 15

N,N'-dibenzylethylenediaminium-N,N'-diacetyl-L-cystinate (Ib; R=PhCH2NH2CH2CH2NH2CH2Ph)

To a 63% solution of N,N'-diacetyl-L-cystine in water (67 mmole, 21.8 g) was added N,N'-dibenzylethylenediamine (67 mmole, 16.0 g). The exothermic reaction gave a slightly oily product which could be recrystallised from water to give 12.0 g (32%) of the title substance as white crystalline needles.

Physical data: Mp 163.8°–165.3° C. $^1$H-NMR (D$_2$O) δ: 2.04 [6H,s,CH$_3$], 2.93 [2H,dd,CH$_2$S], 3.22 [2H,dd,CH$_2$S], 3.44 [4H,s,CH$_2$NBn], 4.27 [4H,s,PhCH$_2$N], 4.47 [2H,dd,CHN], 7.44–7.54 [10H,m,Ph]. $^{13}$C-NMR (D$_2$O) δ: 24.82, 42.82, 45.71, 54.47, 56.99, 132.22, 132.58, 132.67, 133.52, 176.56, 179.80. Analysis (monohydrate): Calcd, C: 53.6, H: 6.6, N: 9.6, S: 11.0. Found, C: 54.5, H: 6.6, N: 9.6, S: 11.2.

Example 16

Di-(1-adamantanaminium)-N,N'-diacetyl-L-cystinate (Ia; R=[C(1) CH(3,5,7) CH2(2,4,6,8,9,10) NH3]

To N,N'-diacetyl-L-cystine (5.35 mmole, 1.73 g) dissolved in 5 mL of water was added 1-adamantanamine (10.7 mmole, 1.61 g). To the solution was dropwise added 60 mL of acetone. The resulting crystalline salt was filtered and dried in vacuo, yielding 2.3 g (67%) of the title compound.

Physical data: Mp 162° C., $^1$H-NMR (D$_2$O) δ: 1.71 [12H, broad dd, CH$_2$(4,6,10)], 1.87 [12H,d,CH$_2$(2,8,9)], 2.05 [6H,s,CH$_3$], 2.17 [6H, broad s, CH(3,5,7)], 2.96 [2H,dd,CH$_2$S], 3.26 [2H,dd,CH$_2$S], 4.50 [2H,dd,CHN]

Example 17

Di-(N-benzyl-2-phenylethylaminium)-N,N'-L-cystinate (Ia; R=PhCH2CH2NH2CH2Ph)

To N,N'-diacetyl-L-cystine (28.7 mmole, 9.3 g) dissolved in 20 mL of water was added N-benzyl-2-phenylethylamine (57.4 mmole, 12.1 g). The solution was concentrated to a thick paste, from which the salt slowly crystallized. The crystalline title compound was isolated and dried.

Physical data: Mp 87° C. $^1$H-NMR (D$_2$O) δ: 2.05 [6H,s,CH$_3$], 2.95 [2H,dd,CH$_2$S], 3.04 [4H,t,PhCH$_2$C], 3.24 [2H,dd,CH$_2$S], 3.33 [4H,t,CH$_2$NBn], 4.25 [4H,s,PhCH$_2$N], 4.49 [2H,dd,CHN], 7.30–7.52 [20H,m,Ph]

Example 18

Piperazinium-N,N'-diacetyl-L-cystinate [Ib; R=NH2(1,4) CH2(2,3,5,6)]

To N,N'-diacetyl-L-cystine (4.60 mmole, 1.49 g) dissolved in 5 mL of water was added piperazine (4.60 mmole, 0.90 g). To the solution was added enough isopropanole to cause formation of an oil, which slowly solidifies. The salt was isolated and dried.

Physical data: Mp>170° C. (dec.) $^1$H-NMR (D$_2$O) δ: 2.05 [6H,s,CH$_3$], 2.96 [2H,dd,CH$_2$S], 3.26 [2H,dd,CH$_2$S], 3.42 [8H,s,CH$_2$(2,3,5,6)], 4.49 [2H,dd,CHN]

Example 19

Di-L-lysinium-N,N'-diacetyl-L-cystinate (Ia; R=H2N(COOH)CH(CH2)4NH3).

N-acetyl-L-cysteine (37 mmol, 6.0 g) and L-lysine (37 mmol, 5.4 g) were dissolved in 10 mL of deionized water. Hydrogen peroxide (18 mmol, 1.5 mL) was added dropwise while stirring, and the temperature was kept below 25° C. The solution was stirred for an additional 4 h. The viscous solution was slowly added to 150 mL of refluxing ethanol containing 0.50 g of crystalline di-L-lysinium-N,N'-diacetyl-L-cystinate. After addition the solution was allowed to cool, and the crystals were filtered off. Washing with ethanol (20 mL), and drying (vacuum, 45° C.) for 24 h afforded 10.0 g (84%) of the title substance as a white crystalline solid.

Physical data: Mp: 208° C.; $[\alpha]^{25}_D = -73°$ (c=0.54, H$_2$O)

We claim:

1. A salt of an organic base and N,N'-diacetyl cystine having the general formula

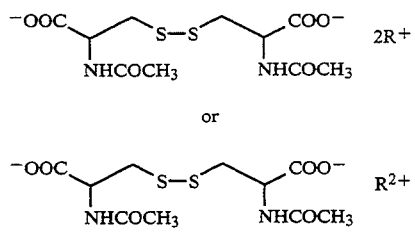

or wherein R+ and R2+ are a mono- and diprotonated amino organic base, respectively, and are selected from the group consisting of lysine, ethylenediamine, N,N'-dibenzylethylenediamine, adamantanamine or N-benzyl-2-phenylethylamine.

2. The salt of claim 1, wherein the N,N'-diacetyl cystine is in the form of its D-isomer, L-isomer, meso-form or racemic mixture.

3. A pharmaceutical composition comprising as active ingredient a salt according to claim 1 in a pharmaceutically acceptable carrier.

4. The composition of claim 3 in solid form as a dry powder formulated for administration from a pressurized metered dose inhaler or from a dry powder.

5. The pharmaceutical composition of claim 3 in the form of a capsule or tablet.

6. The pharmaceutical composition of claim 3 in solution form formulated for administration by nebulization.

* * * * *